United States Patent [19]
Van Den Burg

[11] Patent Number: 5,894,607
[45] Date of Patent: Apr. 20, 1999

[54] URINE COLLECTION DEVICE

[76] Inventor: Anthonius Daniel Van Den Burg, Winkelwaard 219, NL-1824 HP Alkmaar, Netherlands

[21] Appl. No.: 08/716,462

[22] PCT Filed: Mar. 28, 1995

[86] PCT No.: PCT/NL95/00118

§ 371 Date: Oct. 10, 1996

§ 102(e) Date: Oct. 10, 1996

[87] PCT Pub. No.: WO95/26173

PCT Pub. Date: Oct. 5, 1995

[30] Foreign Application Priority Data

Mar. 28, 1994 [NL] Netherlands ............ 9400487

[51] Int. Cl.⁶ .................................................. A47K 11/00
[52] U.S. Cl. .................... 4/144.2; 4/144.1; 383/80
[58] Field of Search ................ 4/144.1–144.4; 383/36, 59, 60, 80

[56] References Cited

U.S. PATENT DOCUMENTS

| | | | |
|---|---|---|---|
| 2,382,276 | 8/1945 | Wells | 4/144.1 |
| 2,875,451 | 3/1959 | Stegeman. | |
| 3,095,578 | 7/1963 | Stanford | 4/144.2 |
| 3,432,865 | 3/1969 | Schwartz | 4/144.3 X |
| 3,568,218 | 3/1971 | Beckman | 4/144.1 |
| 4,290,466 | 9/1981 | Villa et al. | 150/1 |
| 4,296,502 | 10/1981 | Bortle | 4/144.1 |
| 4,531,245 | 7/1985 | Lowd et al. | |
| 4,610,039 | 9/1986 | Stern | 4/144.2 X |
| 5,112,324 | 5/1992 | Wallace. | |
| 5,235,705 | 8/1993 | Belisle. | |
| 5,342,330 | 8/1994 | Kane et al. | 4/144.1 X |
| 5,662,630 | 9/1997 | Raynie | 4/144.2 X |

FOREIGN PATENT DOCUMENTS

| | | |
|---|---|---|
| 0 068 712 | 1/1983 | European Pat. Off. . |
| 0 123 661 | 10/1984 | European Pat. Off. . |
| 2 558 054 | 7/1985 | France . |
| 87 06 405 | 9/1987 | Germany . |
| 90 00 090 | 3/1991 | Germany . |
| 1 311 491 | 3/1973 | United Kingdom . |

*Primary Examiner*—Charles E. Phillips
*Attorney, Agent, or Firm*—Young & Thompson

[57] ABSTRACT

A urine collection means for use by a person of the male sex comprises a flexible container in which the urine can be collected, as well as a closable neck joined onto said container. In order to improve the ease of handling, the neck has a rigid pipe section in which the flexible container can be stored. The end of the pipe section remote from the container is closable by means of a cap, while the container can be stored in the space delimited by the wall of the pipe section and the cap.

11 Claims, 1 Drawing Sheet

U.S. Patent  Apr. 20, 1999  5,894,607
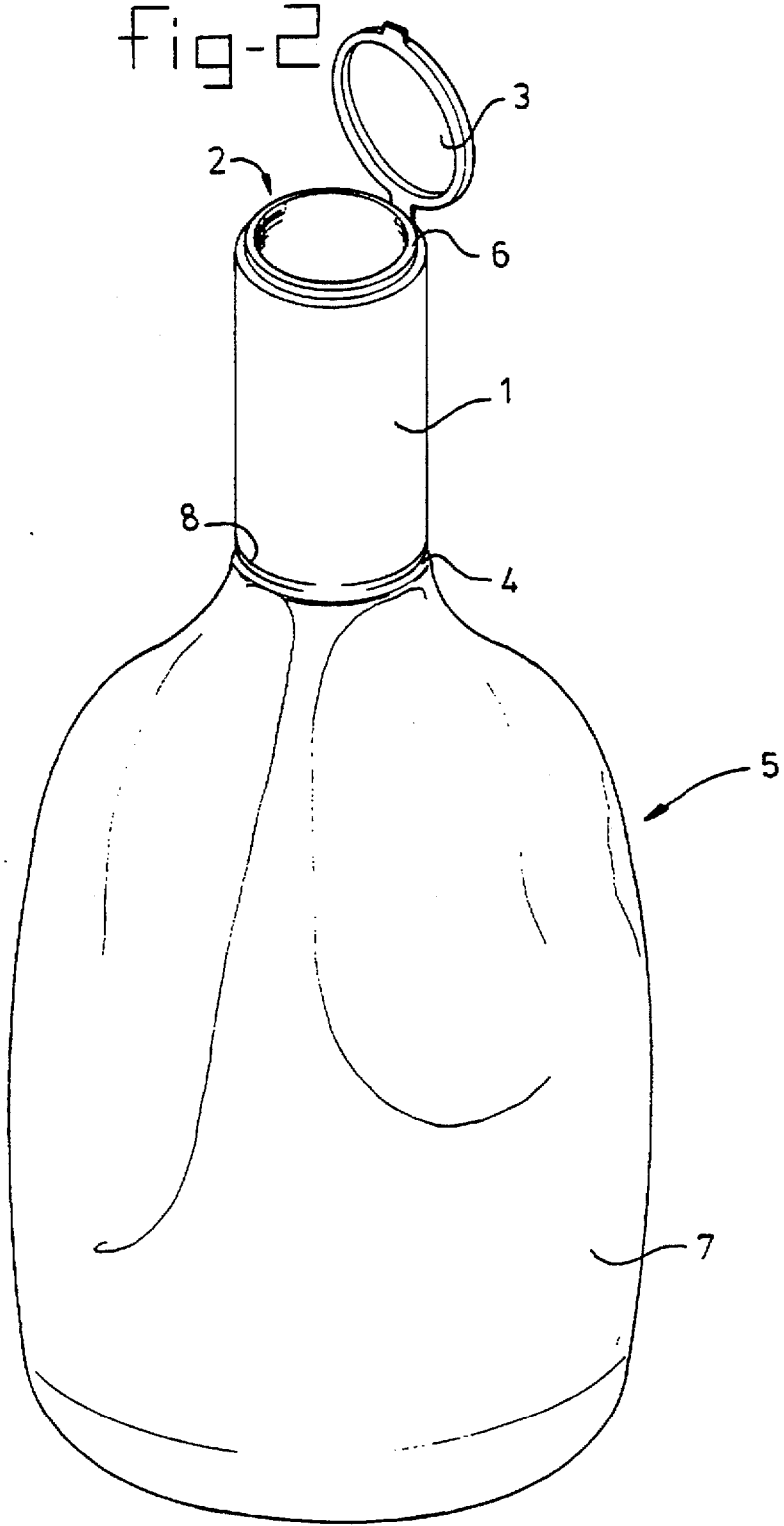

URINE COLLECTION DEVICE

BACKGROUND OF THE INVENTION

1. Field of the Invention

It The invention relates to a urine collection means for use by a person of the male sex, which means comprises a flexible container in which the urine can be collected, as well as a closable neck joined onto said container.

2. Description of the Related Art

Means of this type are disclosed in DE-U-9100090. In the case of this known urine collection means, the container and the neck form a whole made of a flexible plastic This known means has the disadvantage that it is not easy to handle It is true that a reinforcing ring is fitted around the neck, the purpose of which is to increase the dimensional stability of the neck, but this can nevertheless be squashed flat when the neck is held firmly.

The fact that the dimensional stability of the neck is too low makes it not easy for the user to place and to remove the urine collection means in the correct manner. The consequence of this is that spillage can not always be prevented.

This known urine collection means takes up a fairly large volume, even before it has been used, as a result of which it cannot be carried easily and discreetly.

SUMMARY OF THE INVENTION

The aim of the invention is to provide a urine collection means of the type described above which does not have these disadvantages This aim is achieved in that the neck is made up of a rigid pipe section.

The means according to the invention can be firmly held in the region of the rigid pipe section. On the one hand, said pipe section has, in particular, a suitable, round shape which fits easily in the hand. On the other hand, the rigidity can be chosen to be sufficiently high that the pipe section will not be squashed flat even when gripped firmly. A further advantage is that the flexible container can be stored in the rigid pipe section.

Preferably, the pipe section is closable by means of a cap at its end remote from the container and the container can be stored in the space delimited by the wall of the pipe section and the cap. As the urine collection means takes up relatively little space in the state in which the container is stored in the pipe section, it can be carried discreetly.

The cap closes the pipe section air-tight, as a result of which the container is retained reliably in the pipe section.

According to a simple embodiment, the container comprises a bag of flexible material, the entrance to which is determined by a narrowed collar, and the pipe section is a separate pipe section, to which the collar is fined in a liquid-tight manner.

BRIEF DESCRIPTION OF THE DRAWINGS

The invention will be explained in more detail below with reference to an illustrative embodiment shown in the figures.

FIG. 1 shows a perspective view of the urine collection means according to the invention, with the flexible container stored in the pipe section.

FIG. 2 shows a perspective view with the flexible container out of the pipe section ready for use.

DESCRIPTION OF THE PREFERRED EMBODIMENTS

The urine collection means shown in the figures comprises a rigid pipe section 19 for example made of a rigid plastic such as PVC, as wall as a flexible bag 5, for example made of a flexible plastic or rubber, which is attached thereto in a liquid-tight manner it would also be possible for the means to be made of a disposable material, such as, for example, water-tight cardboard for the pipe section, and plasticised paper.

A lid 3 is attached to the pipe section 1 and, for example, can be formed in one piece with the pipe section 1 via an elastic hinge. The lid 3 can be fitted on the periphery 6 of the pipe section 1 in a liquid-tight manner.

The flexible bag 5 is likewise fitted on the pipe section 1 in a liquid-tight manner. Said bag 5 has a narrowed collar 4, fixed by means of the elastic ring 8 on the pipe section 1, and a balloon-shaped section 7, the capacity of which can be, for example, 1 liter.

The rigid pipe section 1 can be held easily during use; when the bag 5 is partly or completely full, it can be closed liquid-tight with the aid of the lid 3.

When the bag 5 is still empty, it can be stored in the pipe section 1 in the manner shown in FIG. 1 When staring the bag 5 in the pipe section 1, the lid 3 must be removed from the pipe section 1, such that the air can be squeezed out of the interior of the bag and the latter can be brought down to a small volume.

The lid 3 is then placed on the pipe section 1 and, by virtue of the tight connection, the bag can be reliably retained in said pipe section 1 between lid 3 and pipe section 1.

I claim:

1. A urine collection device for use by a male person, said device comprising a flexible bag adapted to hold urine, said bag having a narrowed collar and a balloon-shaped section, said collar being attached to a rigid pipe section, a cap for closing said pipe section at its end remote from said collar in a liquid and air tight manner, wherein when in use said cap will retain urine in said collection device and when not in use with said cap removed said balloon-shaped section can be placed in said pipe section and thereafter with said cap in place said balloon-shaped section will be retained in said pipe section by at least in part the air tight nature of said cap.

2. The urine collection device of claim 1, wherein the rigid pipe section comprises rigid plastic.

3. The urine collection device of claim 2, wherein the rigid plastic is PVC.

4. The urine collection device of claim 1, wherein the flexible bag comprises at least one of flexible plastic and rubber.

5. The urine collection device of claim 1, wherein at least one of the rigid pipe section and the flexible bag comprises disposable materials.

6. The urine collection device of claim 5, wherein the rigid pipe section comprises water-tight cardboard.

7. The urine collection device of claim 5, wherein the flexible bag comprises plasticized paper.

8. The urine collection device of claim 7, wherein the rigid pipe section comprises water-tight cardboard.

9. The urine collection device of claim 1, wherein the cap is joined to the rigid pipe section through an elastic hinge.

10. The urine collection device of claim 9, wherein the cap, the rigid pipe section, and the elastic hinge consist of a single piece of material.

11. The urine collection device of claim 1, wherein the rigid pipe section has a restricted circumferential area close to one end, the narrowed collar being adapted to be held in the restricted circumferential area by an elastic element.

* * * * *